United States Patent [19]
Holmovist et al.

[11] Patent Number: 5,198,357
[45] Date of Patent: Mar. 30, 1993

[54] PREPARATION OF A BLOOD PLATELET LYSATE FOR USE IN A CELL CULTURE MEDIUM FOR HYBRIDOMA CELLS

[75] Inventors: Olov Holmovist, Lund; Bengt Westermark, Upsala, both of Sweden

[73] Assignee: Ellco Food AB, Kavlinge, Sweden

[21] Appl. No.: 634,113

[22] PCT Filed: Apr. 26, 1989

[86] PCT No.: PCT/SE89/00232
§ 371 Date: Dec. 26, 1990
§ 102(e) Date: Dec. 26, 1990

[87] PCT Pub. No.: WO89/10398
PCT Pub. Date: Nov. 2, 1989

[30] Foreign Application Priority Data
Apr. 26, 1988 [SE] Sweden ............... 8801537-5

[51] Int. Cl.⁵ ................ C12N 5/00; C12N 1/00
[52] U.S. Cl. ............... 435/240.26; 435/240.1; 435/240.3; 435/243
[58] Field of Search ............ 435/240.1, 240.3, 243, 435/7.21, 240.26

[56] References Cited

U.S. PATENT DOCUMENTS

| | | | |
|---|---|---|---|
| 4,350,687 | 9/1982 | Lipton et al. | 424/177 |
| 4,404,279 | 9/1983 | Ricotti et al. | 435/243 |
| 4,473,552 | 9/1984 | Jost | 435/2 |
| 4,959,308 | 9/1990 | Ogden | 435/7.21 |
| 4,987,079 | 1/1991 | Cullor | 435/240.2 |
| 5,045,467 | 9/1991 | Bertheussen | 435/240.31 |
| 5,045,468 | 9/1991 | Darfler | 435/240.27 |

FOREIGN PATENT DOCUMENTS 0104831  4/1984  European Pat. Off. .

OTHER PUBLICATIONS

*Annual Review of Biochemistry,* vol. 45, 1976, E. E. Snell: "Growth Factors in Mammalian Cell Culture", see in particular p. 540.

Dialog Information Services, File 55 BIOSIS, Dialog Accession No. 0015173922, BIOSIS No. 7909715, Barano, J. L. S. et al., "Serum-Free Medium Enhances Growth and Differentiation of Cultured Pig Granulosa Cells", & Endocorinology 116 (1), 1985, 51-58.

Dialog Information Services, File 351 WPIL, Dialog Accession No. 2971640, WPI Acc No.: 82-19622E/10, (Haematology Blood): "Thrombocyte Concentrate Prodn. for Use in Haemastais Includes Treating Blood or Platelet Rich Plasma with Tetracycline Hydrochloride to Reduce Clumping", & SU 833246, A, 810531, 8210 (Basic).

*Chemical Abstracts,* vol. 95, No. 19, Nov. 9, 1981, (Columbus, Ohio, U.S.), see p. 122, Abstract 162602m, P. D. Phillips et al.: "Growth Regulation of WI138 Cells in a Serum-Free Medium", & Exp. Cell Res. 1981, 134(2), 297-302 (Eng).

*Tips,* vol. 9, Feb. 1988, C. P. Page: "The Involvement of Platelets in Non-Thrombotic Processes" (Elsevier Publications, Cambridge), pp. 66-70.

*Primary Examiner*—David M. Naff
*Assistant Examiner*—Deborah K. Ware
*Attorney, Agent, or Firm*—Cushman, Darby & Cushman

[57] ABSTRACT

A platelet lysate is produced from plasma derived from animal whole blood that contains an added citrate to prevent coagulation of the blood during storage. The lysate is prepared by centrifuging plasma to produce a platelet rich paste, adding calcium to the paste to lyse the platelets therein and coagulate fibrinogen to produce a clear liquid containing lysed platelets, sterile filtering the liquid and collecting a liquid filtrate containing the lysed platelets. The obtained lysate of platelets can be used to wholly or partly replace foetal calf serum in cell culture, such as in culture of hybridoma cells for preparing monoclonal antibodies.

8 Claims, 2 Drawing Sheets

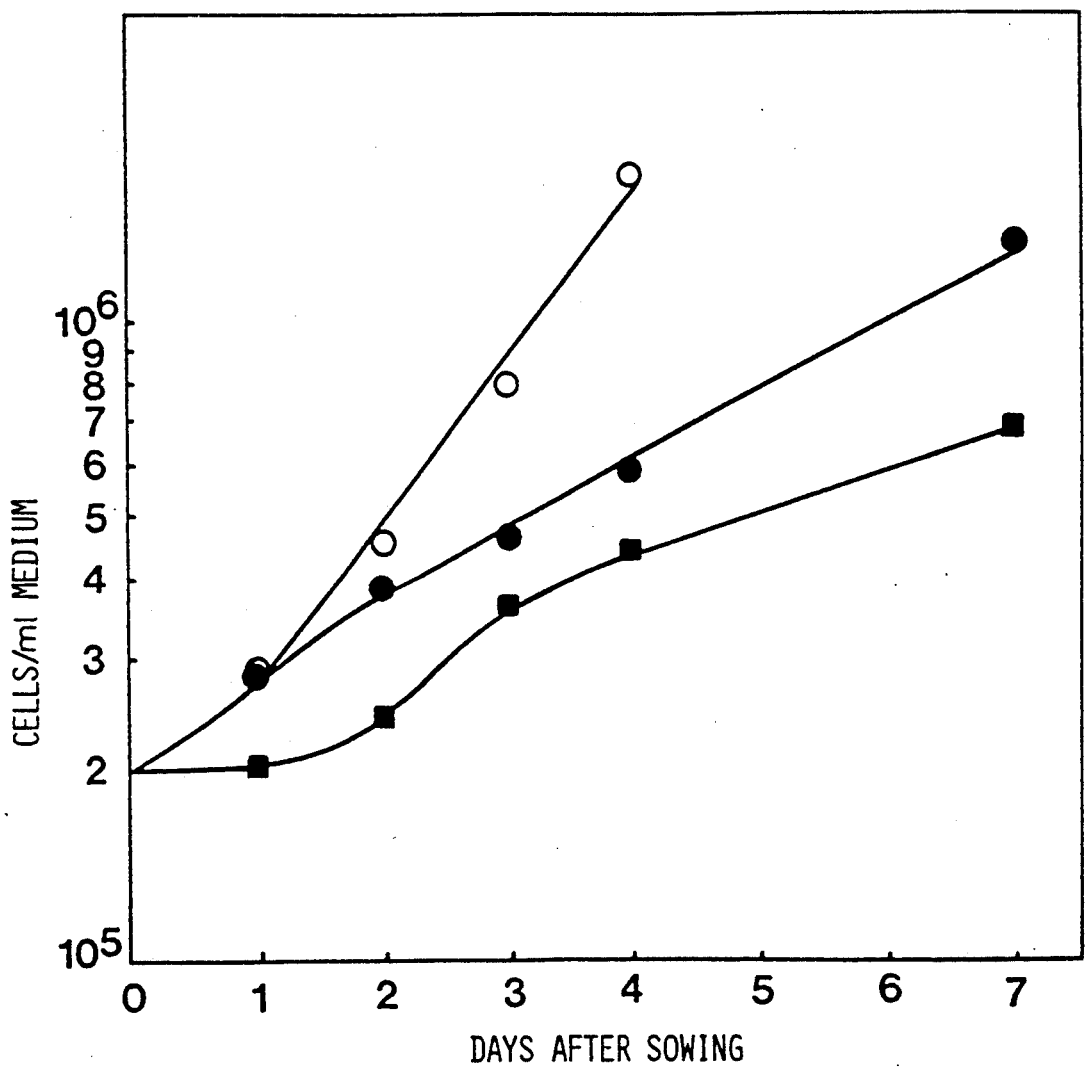
FIG._1

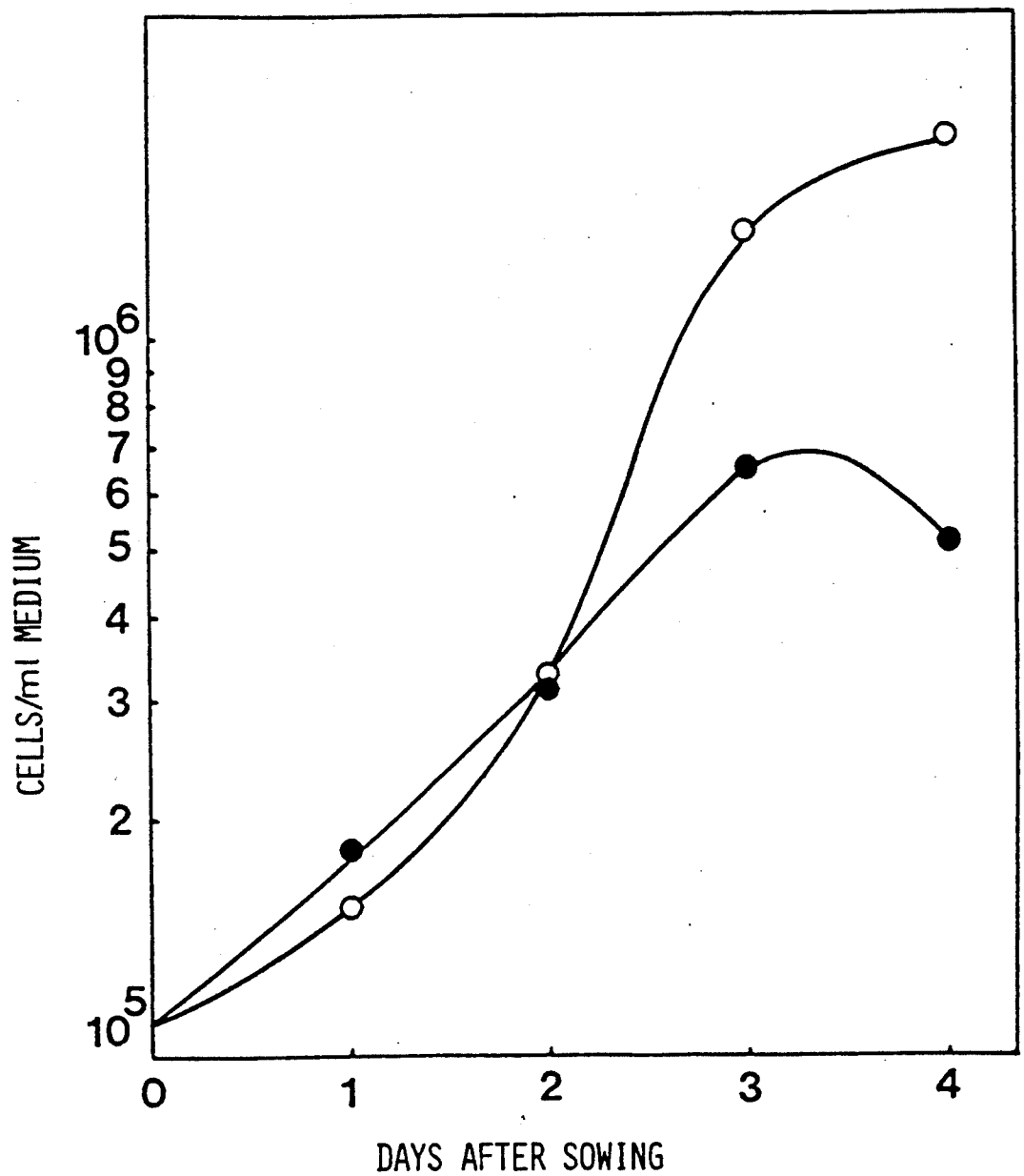
FIG_2

PREPARATION OF A BLOOD PLATELET LYSATE FOR USE IN A CELL CULTURE MEDIUM FOR HYBRIDOMA CELLS

The present invention relates to a blood platelet lysate obtained from plasma from animal whole blood, a method for preparing the blood platelet lysate and a cell culture medium containing the blood platelet lysate.

A problem in the slaughterhouse industry in an international perspective is, in alia, to find a continuous and profitable market for slaughter blood. In many countries, the blood is even discarded as waste material for lack of possibilities of processing or using the blood. In cases where the slaughter blood is taken care of, it is mainly used as an admixture to foodstuffs and animal feed. The hemoglobin part of the blood can be used for different blood products, such as black-pudding, and the plasma part can be used as a thickener, a protein-enriching agent etc. Yet, there are not always marketing possibilities for all slaughter blood, and it is therefore important to find new fields of application.

In biotechnology, a further problem is that along with the ever increasing culture of mammalian cells and other animal cells for production and research, one of the main components of the growth medium, foetal calf serum (FCS), has become a limiting factor. Foetal calf serum (FCS) is extracted from calf foetus from slaughtered cows. There are also other drawbacks: FCS is expensive, and the quality when culturing a special cell line may vary strongly from batch to batch. Large efforts have therefore been made to develop alternatives to FCS.

We have now surprisingly found that the blood platelet fraction in the plasma part in blood is an excellent agent for cell culture, and that it can wholly or partly replace FCS, especially when culturing hybridoma cells.

Many different attempts to find alternatives to FCS are known. In U.S. Pat. No. 4,350,687 the object is to produce a single, simple and well-defined component to promote the growth of tumor cells. The source is platelets from human blood which is outdated and has become unfit for clinical use. This patent specification also states that extracts from platelets can promote the growth of 3T3 cells, SV3T3 cells and mouse fibroblasts which have been transformed. Gospadorowitz and Moran (Ann. Rev. Biochem. 45 (1976) 540) pointed out that the mitogenic factor for 3T3 cells should be present in platelets.

Platelet extracts are also known to stimulate primary cultures from pigs ("Serum-free medium enhances growth and differentiation of cultured pig granulosa cells" Barano J L S; Hammond J M, Milton S, Endocrinology 116 (1), 1985, 51–58), and "skin explants" ("Support and stimulation of epidermal cell outgrowth from porcines skin explants by platelet factors". Hebda PA, Alstadt SP, Hileman WT, Eaglstein WH. Br J Dermatol 1986 Nov; 115(5):529–41).

According to the classical theory, the role of the platelets is to aggregate on the site of the injury, to form a plug and to empty their contents of growth factors and other mediators, so as to stimulate connective tissue to grow, migrate and heal the wound, and to stimulate vascularisation.

A further attempt is stated in European patent specification 0,104,831. Here the starting material is material that normally goes to waste in slaughter, viz. "tissue juices together with flowing blood, a semi-solid, rubbery mass". The efficiency of this product is again demonstrated on cells which can be expected to respond in accordance with the classical theory: WI-38 (human fibroblasts); and on cell line VerO from African monkey kidney (transformed cells).

These previous attempts have all concerned either transformed cells or cells on which platelets can act in accordance with the classical theory.

The idea that platelets can play a role other than indicated by the classical theory, was recently suggested (Page, C.P. TIPS 9 (1988) 66–71). However, nowhere in this paper is it indicated that platelets or their contents stimulate the growth and division of cells which have been obtained from the immunological system.

The present invention is based on the unexpected and surprising result that a platelet extract stimulates the growth and division of cells from the immunological system, viz. hybridoma cells in which the original two components—the B-cell and the leukaemia cell—are both derived from the immunological system. Moreover, it is shown that the production of monoclonal antibodies in hybridoma cells which have been cultured in the product according to the present invention, may be well compared with the one obtained when hybridoma cells are cultured in FCS. Finally, the present invention shows that the platelet product functions poorly for a number of transformed cells, which goes to show that the demonstrated effect cannot be a general growth-promoting effect of platelets on transformed cells.

Common substitutes for FCS are serum-free, synthetic media containing various growth factors and, in many cases, e.g. transferrin and insulin. When FCS is used, the added amount is usually between 1 and 20%, in many cases 10% (% by volume). The remaining component is a nutrient medium containing salts and amino acids. On an industrial scale, serum-free media are frequently preferred for economical reasons.

One object of the present invention is to provide a concentrated platelet lysate which has been obtained from plasma from animal whole blood, young as well as adult animals, and which wholly or partly can replace FCS in cell culture media.

A further object of the present invention is to provide a method for preparing said platelet lysate.

A still further object of the present invention is to provide a cell culture medium containing said platelet lysate, a conventional nutrient medium and, optionally, FCS.

According to the present invention, a platelet lysate for use in cell culture is provided, characterised in that it is prepared from plasma from whole blood from slaughter animals, and that it consists mainly of lysed platelets.

Furthermore, there is provided a method for preparing a platelet lysate derived from plasma from animal whole blood to which a citrate has been added to avoid coagulation, the plasma being of food quality and having a hemolysis figure of about 1-3, characterised in a) that said plasma is centrifuged so as to obtain a platelet-rich paste,
b) that $Ca^{2+}$ is added to said paste, in equimolar amounts in relation to the citrate content in the original plasma, for lysing the included platelets and coagulating the remaining components, a clear, light red liquid of lysate which to a substantial degree consists of lysed platelets, and a coagulate being obtained,
c) that said clear, light red liquid is sterile-filtered, and
d) that the platelet lysate thus obtained is collected.

Further there is provided a cell culture medium characterised in that it contains
a) a platelet lysate which has been prepared from plasma from whole blood from slaughter animals and consists mainly of lysed platelets,
b) a conventional nutrient substrate, and
c) optionally, foetal calf serum, and use thereof for culture of hybridoma cells.

The animals which are intended according to the present invention can, in principle, be all animals, young or adult, from which the required amount of platelets can reasonably be collected. Use is preferably made of blood from mainly adult animals, since this is more economical. Examples of suitable animals are slaughter animals and other farmbred animals such as cattle, pigs, sheep or poultry. Preferably, use is made of whole blood from cattle or pigs, most advantageously cattle.

The cell culture medium according to the present invention has appeared to be especially useful for culturing hybridoma cells which are today used to produce monoclonal antibodies. The present cell culture medium can, wholly or partly, replace foetal calf serum.

Below follows a detailed description of preferred embodiments of the present invention.

For preparing the present platelet lysate, use is made of whole blood from animals, such as slaughter cattle or pigs. The animals should be healthy and satisfy the requirements that are put forward in veterinary inspection of animals intended for foodstuffs according to Swedish regulations, as well as under EEC and US rules.

After drawing off, the blood is cooled rapidly, preferably to about +4° C. within a minute. A citrate, such as sodium citrate, is added to prevent coagulation. Optionally, the blood is then stored in cooling tanks until it is time for further treatment.

Subsequently, the blood is examined, both in bacteriological and in sensory respect. The blood should preferably satisfy the requirements which the National Food Administration places on products intended for foodstuffs, and moreover the blood should satisfy the corresponding regulations within the EEC and the US. From experience, we have found that suitable upper limits for the bacterial content in blood are those stated in Table I below. The sensor analysis is carried out as follows: one smells the blood and by experience decides whether the blood is acceptable or not.

Bacteriological samples are preferably taken both from whole blood and from separated plasma.

TABLE I

| BACTERIOLOGICAL LIMIT OF ACCEPTANCE | |
|---|---|
| | Number of bacteria/ml |
| Aerobic number of bacteria (tryptonglucose extract agar 30° for 3 days) | <100,000 |
| Thermostable *coli* (VGR-agar 44° for 1 day) | <300 |
| Tellurite-resistent *enterococci* (Slanetz-Bartley agar 37° for 2 days) | <3,000 |
| DNAs-positive *staphylococci* (Baird-Parker agar 37° for 2 days) | <300 |

TABLE I-continued

| BACTERIOLOGICAL LIMIT OF ACCEPTANCE | |
|---|---|
| | Number of bacteria/ml |
| Occurrence of *salmonellae* (Enrichment broth-SS agar) | negative |

Based on the results from examination and analysis, it is decided whether the blood can be used or not. The blood is separated into plasma and red blood corpuscles. Use is preferably made of a blood separator; but also other suitable, traditional separators can be used. All the time the blood is kept cool, preferably at about +4° C. From the whole blood, a separate sample is taken for hemolysis assessment of the plasma part. The hemolysis figure is a measure of the amount of lysed red blood corpuscles. A preferred method of measuring the hemolysis figure is ocular assessment of the colour of the plasma by comparison with a colour chart. The colour values on this chart are shown in Table II. Colour measuring is suitably made on samples after table centrifuging in test tubes. The plasma used in the present method has a hemolysis figure of 1-3, preferably 1-2 and most preferred 1.

TABLE II

| COLOUR MEASURING OF BOVINE PLASMA (PHOTO) | | | |
|---|---|---|---|
| Hemolysis figure | L* (lightness) | a* (redness) | b* (yellowness) |
| 1 | 35.44 | 13.20 | 39.12 |
| 2 | 26.98 | 18.85 | 26.14 |
| 3 | 21.59 | 20.27 | 16.58 |
| 4 | 17.91 | 22.09 | 11.54 |
| 5 | 16.32 | 19.83 | 7.35 |
| 6 | 12.74 | 15.47 | 4.09 |
| 7 | 11.52 | 9.69 | 1.67 |
| 8 | 11.59 | 6.50 | 0.23 |

L* = lightness; lighter the higher the value
a* = redness; redder the higher the value
b* = yellowness; more yellow the higher the value Instruments and Measuring Conditions Hunterlab Color Quest
Colour Chart: CIELAB (1976)
Illuminant D65, 10° standard observer, specular excluded
Measuring opening: 6 mm diameter, white background Then the platelet fraction was concentrated from the plasma. This is preferably carried out in that the plasma is first centrifuged to about 100-fold concentration, and subsequently this concentrate is further concentrated by a second centrifugation. Now a solid phase of concentrated platelets is obtained. To this solid phase there are added $Ca^{2+}$ ions, for example in the form of $CaCl_2$, in an equimolar amount in relation to the citrate content of the original plasma. The addition of $Ca^{2+}$ causes fibrinogen, etc., to coagulate and the platelets to lyse, which gives a clear, light red top liquid. This clear liquid is sterile-filtered, and the platelet lysate is ready for use.

The method can be a continuous method, a batchwise method or a combination of these. If desired, several concentration steps, such as a centrifugation step, a filtration step or some other analogous step, can be introduced.

The platelet lysate according to the present invention consists mainly of lysed platelets, especially about 90-100% by volume, most preferred about 95-100% by volume.

The cell culture medium according to the present invention contains, in addition to the present platelet lysate, a nutrient medium containing salts etc and, optionally, FCS. The nutrient medium can be any suitable, conventional nutrient medium, e.g., one stated in the Sigma catalogue issued by Sigma Chemical Company.

The amount of FCS which is optionally added is not critical, but is selected as required and desired. For economical reasons, it is frequently desired to minimize the amount of FCS used, but for different other reasons, an addition may be required.

For the purpose of further describing the advantages and purposes of the present invention, a number of nonlimiting Examples are stated below.

In all Examples, the platelet lysate according to the present invention is designated "S". The FCS used has been supplied by Gibco.

Example 1 states a preferred method for preparing a platelet lysate according to the present invention.

EXAMPLE 1

From a continuous process for separating plasma from whole blood from slaughter cattle, about 1 ton of plasma was taken. A bacteriological examination of the whole blood yielded the following values:

A sensory and bacteriological analysis yielded an acceptable result. The yield of plasma from whole blood is about 60%. Thus, the amount of plasma obtained corresponds to about 1.7 ton of blood. The plasma had a hemolysis figure of 2. A bacteriological examination was also made of the plasma which was found to be acceptable.

First the plasma was centrifuged in a so-called bactofuge (Alfa Laval type D 3187 M) for 15 minutes. 5734 g of cell-rich plasma was obtained, which was centrifuged at 925 g in a Mistral 6 1 at 4° C. The obtained gel-like paste, 127 g, which was white to red coloured, was collected.

63.5 g of water was added to the paste (1:0.5, weight:weight, paste:water) and the mixture was stored in a refrigerator at 4° C. for 15 minutes. After 15 minutes, 127 g of 0.024M $CaCl_2$ was added (equimolarly in relation to the citrate content in the blood), and the sample was centrifuged directly at 1900 g in a Mistral 6 1 at 4° C.

The supernatant, which was red to whitish, was collected and combined with the liquid that was included in the paste after the second centrifugation at 1900 g. The liquid from the paste was extracted in that the paste was transferred to a Büchner funnel with a fixed sieve plate, and was agitated by a spoon until all liquid had been extracted. The total amount of liquid was 176 g.

The total volume of liquid (176 g) was then filtered through two Millipore filters; first through a filter under the name of Milligord TP, catalogue No. CW 004 T4, and then through a sterile filter, Millipack ™ 200, catalogue No. MPGL 20C A3. Before filtration, the filters were soaked with distilled water. Total amount of filtrate: 157 g.

The filtration was carried out between 0.5 and 4 bar. The sterile liquid which is the final product, was filtered down into sterile polypropylene flasks Nalge 2106, and the flasks were stored at 4° C.

Table III presents a sampling schedule for the experiment, and Table IV gives the results of analysis in the analysis positions as stated. The analyses have been carried out at the Agricultural University of Sweden, Faculty of Veterinary Medicine, Institute of Clinical Chemistry, P.O. Box 7038, 750 07 Uppsala.

TABLE III

SAMPLING SCHEDULE FOR THE ANALYSIS

| | | Analysis position |
|---|---|---|
| Whole blood | Centrifugation | 1 |
| Plasma | Bactofugation | 2 |
| Cell-rich plasma | Centrifugation 925 g | 3 |
| Paste | Lysing $H_2O$ $CaCl_2$ | |
| — | Centrifugation 1900 g | 4 |
| Supernatant | Filtration | 5 |
| Sterile product | | 6 |

TABLE IV

RESULT OF THE ANALYSIS

| Analysis position | Blood leucocytes Conc. of particles × $10^9$/L | Platelets Conc. of particles × $10^9$/L | Erythrocytes Conc. of particles × $10^{12}$/L | Protein % by weight |
|---|---|---|---|---|
| 1 | 5.6 | 296 | 7.85 | 17.9 |
| 2 | 0.3 | 154 | 0.02 | 7.1 |
| 3 | 0 | 370 | 0 | 6.2 |
| 4 | 0 | 24 | 0 | 3.8 |
| 5 | 0 | 15 | 0 | 2.0 |
| 6 | 0 | 12 | 0 | Not analysed |

The method can be optimized by e.g. further centrifugation and filtration so as to increase the yield and quality of the final product. Also other steps of concentrating which can be compared to centrifugation and filtration and are based on, for example, the affinity principle, may be used.

Examples 2 and 3 below concern culture experiments with hybridoma cells, in which the adding of FCS only, (for comparison purposes) to a nutrient medium (Dulbecco's min. medium, Gibco) has been compared with the adding of a mixture of FCS and the present platelet lysate in different percentages.

The concentrations of FCS or FCS+S are stated in % by volume of the total volume of cell culture medium.

EXAMPLE 2

8F4 hybridoma cells were cultured (37° C. in 8% $CO_2$), and the cells were counted in a Bürker chamber on day 2, 3, 4, 5 and 6.

The cells have first been adapted to the S-supplement by being cultured for about 2 weeks in a medium containing 1% FCS +1% S-supplement. The experiments were here carried out in single samples.

| | \multicolumn{6}{c}{Number of cells per ml × $10^6$} |
|---|---|---|---|---|---|---|
| | FCS 10% | FCS 1% | FCS 5% | FCS + S 1 + 5% | FCS + S 1 + 1% | FCS + S 1 + 0.2% |
| 8F4 hybridoma | | | | | | |
| Day 2 | 0.72 | 0.36 | 0.38 | 0.59 | 0.46 | 0.40 |
| Day 3 | 1.38 | 0.61 | 0.64 | 1.06 | 0.78 | 0.62 |
| Day 4 | 1.93 | 0.94 | 1.12 | 1.52 | 1.04 | 0.92 |
| Day 5 | 2.88 | 1.11 | 1.28 | 1.72 | 1.33 | 1.08 |
| Day 6 | 2.51 | 1.22 | 1.58 | 1.98 | 1.22 | 1.26 |

EXAMPLE 3

SK4H hybridoma cells were cultured and counted as in Example 2.

|  | FCS 10% | FCS 1% | FCS 5% | FCS + S 1 + 5% | FCS + S 1 + 1% | FCS + S 1 + 0.2% |
| --- | --- | --- | --- | --- | --- | --- |
| SK4H hybridoma |  |  |  |  |  |  |
| Day 2 | 0.86 | 0.30 | 0.52 | 0.61 | 0.43 | 0.27 |
| Day 3 | 2.70 | 0.82 | 1.50 | 1.83 | 1.24 | 1.06 |
| Day 4 | 3.58 | 1.06 | 1.90 | 2.72 | 2.00 | 1.48 |
| Day 5 | 3.34 | 1.44 | 2.05 | 2.52 | 1.97 | 1.70 |
| Day 6 | 2.24 | 1.26 | 1.54 | 2.11 | 1.03 | 1.18 |

Number of cells per ml $\times 10^6$

Examples 2 and 3 clearly show that the platelet lysate according to the present invention is an excellent substitute for FCS. As appears, an admixture of 10% FCS can substantially be replaced by an admixture of 1% FCS and 5% of the present platelet lysate.

Examples 4, 5 and 6 concern culture experiments with 8F4 hybridoma cells in Dulbecco's min. medium (Gibco) with additions of FCS, the present platelet lysate (S) or mixtures thereof. The present platelet lysate has been inactivated at 56° C. for 30 minutes and, respectively, has not been inactivated. The cells have been placed in cell culture plates, in an original concentration of 50,000 cells/ml (Examples 4 and 5) or in culture flasks in a cell concentration of 75,000 cells/ml (Example 6).

EXAMPLE 4

|  | FCS 10% | FCS 1% | S 15% | S 5% | FCS + S 1 + 5% | FCS + S 1 + 1% |
| --- | --- | --- | --- | --- | --- | --- |
| Day 2 | 0.232 | 0.072 | 0.177 | 0.120 | 0.290 | 0.960 |
| Day 3 | 0.590 | 0.085 | 0.430 | 0.195 | 0.464 | 0.180 |
| Day 4 | 1.205 | 0.155 | 0.665 | 0.375 | 0.915 | 0.285 |
| Day 5 | 1.510 | 0.250 | 1.525 | 0.515 | 1.045 | 0.480 |
| Day 6 | 1.355 | 0.315 | 1.590 | 0.695 | 0.965 | 0.280 |

Inactivated S

EXAMPLE 5

|  | FCS 10% | FCS 1% | S 15% | S 5% | FCS + S 1 + 5% | FCS + S 1 + 1% |
| --- | --- | --- | --- | --- | --- | --- |
| Day 1 | 0.056 | 0.037 | 0.060 | 0.036 | 0.072 | 0.064 |
| Day 2 | 0.236 | 0.076 | 0.280 | 0.130 | 0.230 | 0.112 |
| Day 3 | 0.680 | 0.100 | 0.450 | 0.280 | 0.485 | 0.200 |
| Day 4 | 0.985 | 0.155 | 0.630 | 0.370 | 0.815 | 0.280 |
| Day 5 | 1.695 | 0.200 | 1.290 | 0.675 | 1.020 | 0.590 |
| Day 6 | 1.405 | 0.280 | 1.390 | 0.775 | 0.965 | 0.445 |

Not inactivated S

EXAMPLE 6

|  | FCS 10% | FCS 1% | FCS + S 1 + 15* | FCS + S 1 + 5* | FCS + S 1 + 1* | FCS + S 1 + 15 | FCS + S 1 + 5 | FCS + S 1 + 1 |
| --- | --- | --- | --- | --- | --- | --- | --- | --- |
| Day 4 | 1.76 | 0.19 | 1.47 | 1.07 | 0.48 | 1.68 | 1.06 | 0.55 |
| Day 5 |  |  |  |  |  |  |  |  |
| Day 6 | 2.52 | 0.32 | 2.17 | 1.68 | 0.73 | 2.01 | 1.64 | 0.76 |

Culture in flasks

*inactivated

As appears again from Examples 4–6, 1% FCS +5% S constitute an acceptable alternative to 10% FCS. Moreover, 15% S can completely replace 10% FCS. If further appears that an inactivation of S does not affect the growth of cells.

EXAMPLE 7

Culture experiments with FCS and S (inactivated), respectively, on 2F6 hybridoma cells. The cells were placed in an original concentration of 50,000 cells/ml.

|  | FCS 10% | FCS 1% | S 15% | S 5% | FCS + S 1 + 5% | FCS + S 1 + 1% |
| --- | --- | --- | --- | --- | --- | --- |
| Day 1 | 0.049 | 0.027 | 0.042 | 0.044 | 0.052 | 0.040 |
| Day 2 | 0.173 | 0.041 | 0.136 | 0.109 | 0.157 | 0.092 |
| Day 3 | 0.433 | 0.089 | 0.339 | 0.232 | 0.301 | 0.156 |
| Day 4 | 0.890 | 0.092 | 0.707 | 0.409 | 0.583 | 0.238 |
| Day 5 | 1.473 | 0.111 | 1.386 | 0.602 | 0.975 | 0.440 |
| Day 6 | 1.660 | 0.158 | 1.775 | 0.810 | 1.132 | 0.414 |

This Example again shows that 1% FCS +5% S can substantially replace 10% FCS. This also applies to 15% S.

Examples 8, 9 and 10 concern the production of antibodies (Ab) from hybridoma cells in different concentrations of FCS, S and, respectively, mixtures thereof.

Experimental conditions: ELISA plates were coated with sorbent-purified anti-mouse IgG antibodies (10 µg/ml), and hybridoma supernatants were added in serial dilution. Bound mouse antibodies were detected by addition of ALP-conjugated anti-mouse IgG and substrates (paranitrophenyl sulphate). The experiments were carried out in duplicate samples, and determinations of the concentration were obtained by comparison with a known standard of mouse IgG cord parallel in each test run.

EXAMPLE 8

Production of antibodies from 8F4 hybridoma cells cultured in different concentrations of FCS and S. The supernatants on day 5 were measured.

| Test | Hyb/Day | FCS | S | Amount of Ab (µg/ml) |
| --- | --- | --- | --- | --- |
| 1 | 8F4 5 | 10% | — | 10.62 |
| 2 | 8F4 5 | 1% | — | 3.25 |
| 3 | 8F4 5 | — | 5% | 10.00 |
| 4 | 8F4 5 | 1% | 5% | 11.50 |
| 5 | 8F4 5 | 1% | 1% | 5.47 |
| 6 | 8F4 5 | 1% | 0.2% | 4.53 |

EXAMPLE 9

Production of antibodies from 8F4 hybridoma cells cultured in different concentrations of FCS and S. Supernatants on day 6 were measured.

| Test | Hyb/Day | FCS | S | Amount of Ab (µg/ml) |
| --- | --- | --- | --- | --- |
| 1 | 8F4 6 | 10% | — | 6.25 |
| 2 | 8F4 6 | 1% | — | 1.56 |
| 3 | 8F4 6 | 1% | 15% ia | 7.44 |
| 4 | 8F4 6 | 1% | 5% ia | 8.12 |
| 5 | 8F4 6 | 1% | 1% ia | 2.44 |
| 6 | 8F4 6 | 1% | 15% | 8.15 |

-continued

| Test | Hyb/Day | FCS | S | Amount of Ab (µg/ml) |
|------|---------|-----|-----|----------------------|
| 7 | 8F4 6 | 1% | 5% | 8.44 |
| 8 | 8F4 6 | 1% | 1% | 2.06 |

The tests show a slightly higher production of antibodies in cultures with 1% FCS +5% S as compared to cultures with 10% FCS.

EXAMPLE 10

Production of antibodies from SK4H hybridoma cells in FCS and S. The supernatants on day 5 were measured, but supernatants from day 3 indicate a similar tendency, but with lower total concentrations.

| Test | Hyb/Day | FCS | S | Amount of Ab (µg/ml) |
|------|---------|-----|------|----------------------|
| 1 | SK4H 5 | 10% | — | 13.75 |
| 2 | SK4H 5 | 1% | — | 9.63 |
| 3 | SK4H 5 | — | 5% | 17.31 |
| 4 | SK4H 5 | 1% | 5% | 20.78 |
| 5 | SK4H 5 | 1% | 1% | Not assessable |
| 6 | SK4H 5 | 1% | 0.2% | 12.50 |

The SK4H hybridoma produced slightly higher amounts of antibody, which conforms to previous observations made on several occasions. Here, too, the platelet lysate (S) according to the present invention (5%) seems to have a favourable effect on the production of antibodies as compared to culture in FCS only.

Since the present platelet lysate can be obtained from slaughter animals, both adult and young animals, essential advantages in respect of economy and availability are obtained.

Thus, it has surprisingly appeared that the hybridoma cells grow and produce antibodies in a most satisfactory fashion in the present platelet lysate.

Different types of cell necessitate different specific conditions of culture, which means that it is not possible to safely determine whether a certain type of cell grows in a satisfactory manner in a certain type of medium.

In order to elucidate this, experimental cultures of different tumour cells were made in a nutrient medium to which FCS and the present platelet lysate (S) were added. These experiments are accounted for in Examples 11 and 12.

EXAMPLE 11

HL-60 cells (Human promyeloic leukaemia) were cultured in a suspension culture with the nutrient medium RPMI 1640 (Gibco)+antibiotics (penicillin 50 IU/ml and streptomycin 50 µg/ml) and 10% FCS. The cultures were incubated at 37° C. in humid atmosphere of 5% $CO_2$ in air. When the cells had reached the flat phase, a new culture (1st passage) was made with 10% of the platelet lysate (S) according to the present invention under the same conditions, and then a 2nd passage with 10% S. The cells were counted in a Bürker chamber. The results are stated in FIG. 1 in which an unfilled ring (○) concerns experiments with 10% FCS, a filled ring (●) the 1st passage with 10% S, and a filled square (■) the 2nd passage with 10% S. All points constitute an average value of two measurements.

The results show quite clearly that the platelet lysate according to the present invention is not suited as a medium in culturing this type of tumour cells.

EXAMPLE 12

In this experiment, $L1210_{D20}$ (DL-α-difluoromethylornithine-resistant mouse-leukaemia cell line) was cultured in a suspension culture with the same nutrient medium as in Example 11 plus 50 µM β-mercaptoethanol and 20 mM α-difluoromethylornithine.

The results are stated in FIG. 2 in which the same designations are used as in Example 11. Only the 1st passage with 10% S was carried out. Nor did this cell line grow acceptably in the presence of the platelet lysate according to the present invention.

According to the present invention, there is thus provided a platelet lysate for cell culture, said platelet lysate being able to replace, wholly or partly, foetal calf serum and, accordingly, considerably improve the economy and availability of the culture medium.

According to the present invention, also a new and profitable use of animal whole blood is obtained.

We claim:

1. A method for preparing a blood platelet lysate from plasma derived from animal whole blood to which a citrate has been added to avoid coagulation during storage of the blood, which method comprises:
   a) centrifuging said plasma so as to obtain a platelet rich paste,
   b) adding $Ca^{2+}$ to said paste, in equimolar amounts in relation to the citrate content in the centrifuged plasma to lyse the platelets in said paste and to coagulate fibrinogen to produce a clear, light red liquid consists essentially of lysed platelets,
   c) sterile-filtering said clear, light red liquid to produce a liquid filtrate, and
   d) collecting the liquid filtrate which consists essentially of lysed platelets.

2. The method according to claim 1, wherein said liquid filtrate contains about 90-100% by volume of lysed platelets.

3. The method according to claim 1 or 2, wherein said plasma is of food quality and has a hemolysis figure of 1-3, preferably 1-2.

4. The method according to claim 1 wherein in step a), said plasma is centrifuged in a bactofuge to yield a concentrate of about 100-fold concentration, and the resulting concentrate then being centrifuged a second time to yield a further concentration to said paste.

5. The method of claim 1 wherein the platelet lysate produced is combined with a nutrient substrate to produce a cell culture medium.

6. The method of claim 5 wherein the cell culture medium is used to culture hybridoma cells by contacting hybridoma cells with the culture medium.

7. A cell culture medium produced by the method of claim 5.

8. The cell culture medium of claim 7 wherein said medium also contains foetal calf serum.

* * * * *